United States Patent
Shimose (10) Patent No.: US 11,618,704 B2
(45) Date of Patent: Apr. 4, 2023

(54) SYSTEM AND METHOD FOR TREATING EXCREMENT OF LIVESTOCK

(71) Applicant: SHIMOSE MICROBES LABORATORY CORPORATION, Tokyo (JP)

(72) Inventor: Shinichi Shimose, Tokyo (JP)

(73) Assignee: Shimose Microbes Laboratory Corporation, Tokyo (JP)

( * ) Notice: Subject to any disclaimer, the term of this patent is extended or adjusted under 35 U.S.C. 154(b) by 0 days.

(21) Appl. No.: 17/285,676

(22) PCT Filed: Oct. 24, 2019

(86) PCT No.: PCT/JP2019/041706
§ 371 (c)(1),
(2) Date: Apr. 15, 2021

(87) PCT Pub. No.: WO2020/085433
PCT Pub. Date: Apr. 30, 2020

(65) Prior Publication Data
US 2021/0395126 A1    Dec. 23, 2021

(30) Foreign Application Priority Data
Oct. 25, 2018    (JP) .............................. JP2018-200659

(51) Int. Cl.
*C02F 11/02* (2006.01)
*C02F 11/13* (2019.01)
(Continued)

(52) U.S. Cl.
CPC ................ *C02F 11/02* (2013.01); *B09B 3/40* (2022.01); *C02F 11/13* (2019.01); *C10L 5/42* (2013.01);
(Continued)

(58) Field of Classification Search
CPC ...... C02F 11/02; C02F 11/13; C02F 2103/20; C02F 11/06; C02F 2301/063;
(Continued)

(56) References Cited

U.S. PATENT DOCUMENTS 4,750,454 A * 6/1988 Santina .................... F02B 43/08
123/3
5,079,852 A * 1/1992 Nakayama .............. C02F 11/13
34/526
(Continued)

FOREIGN PATENT DOCUMENTS

CN    102564095 A    7/2012
JP    S58-119398 A    7/1983
(Continued)

OTHER PUBLICATIONS

JP-2005257211-A_English (Year: 2005).*
JP 2007-319738A_English (Year: 2007).*
JP 2010-236731 A_English Translation (Year: 2010).*

*Primary Examiner* — Youngsul Jeong
(74) *Attorney, Agent, or Firm* — Locke Lord LLP; James E. Armstrong, IV; Nicholas J. DiCeglie, Jr.

(57) ABSTRACT

A system for treating excrement of livestock includes: reduced-pressure fermentation drying equipment configured to store excrement of livestock in an airtight container, heat and stir the excrement of livestock under reduced pressure so that a temperature of the excrement of livestock is within a predetermined temperature range, decompose organic components of organic matter using microorganisms, and obtain volume-reduced dried product; and heat source equipment that is provided on a downstream side of the reduced-pressure fermentation drying equipment and generates a heat source by combusting the obtained volume-reduced dried product.

8 Claims, 4 Drawing Sheets

(51) Int. Cl.
*B09B 3/40* (2022.01)
*C10L 5/42* (2006.01)
*C10L 9/08* (2006.01)
*C10L 9/10* (2006.01)
*C12M 1/00* (2006.01)
*C12M 1/34* (2006.01)
*C02F 103/20* (2006.01)

(52) U.S. Cl.
CPC ............... *C10L 9/08* (2013.01); *C10L 9/10* (2013.01); *C12M 41/40* (2013.01); *C12M 47/14* (2013.01); *C12M 47/20* (2013.01); *C02F 2103/20* (2013.01); *C10L 2200/0469* (2013.01); *C10L 2290/06* (2013.01); *C10L 2290/08* (2013.01); *C10L 2290/24* (2013.01); *C10L 2290/26* (2013.01)

(58) Field of Classification Search
CPC .... C02F 2301/08; C02F 2303/10; B09B 3/40; B09B 3/00; C10L 5/42; C10L 9/08; C10L 9/10; C10L 2200/0469; C10L 2290/06; C10L 2290/08; C10L 2290/24; C10L 2290/26; Y02E 50/10; Y02E 50/30
See application file for complete search history.

(56) References Cited

U.S. PATENT DOCUMENTS

| | | | |
|---|---|---|---|
| 6,254,775 B1* | 7/2001 | McElvaney | C12M 25/06 210/603 |
| 7,001,512 B1* | 2/2006 | Newsome | C02F 11/185 210/259 |
| 2002/0079266 A1* | 6/2002 | Ainsworth | C12M 45/20 210/603 |

FOREIGN PATENT DOCUMENTS

| | | | | |
|---|---|---|---|---|
| JP | 2005-257211 A | | 9/2005 | |
| JP | 2005257211 A | * | 9/2005 | ............... F23G 7/00 |
| JP | 2007-319738 A | | 12/2007 | |
| JP | 2007319738 A | * | 12/2007 | ............... B09B 3/00 |
| JP | 4153685 B2 | | 9/2008 | |
| JP | 2010-236731 A | | 10/2010 | |
| JP | 2010236731 A | * | 10/2010 | ............... F26B 17/20 |
| JP | 2011-105816 A | | 6/2011 | |
| WO | WO-2006116658 A2 | * | 11/2006 | ............... B09B 3/00 |
| WO | 2019/044996 A1 | | 3/2019 | |
| WO | 2019/058928 A1 | | 3/2019 | |

* cited by examiner

SYSTEM AND METHOD FOR TREATING EXCREMENT OF LIVESTOCK

TECHNICAL FIELD

The present invention relates to a system and a method for treating excrement of livestock such as cows and pigs.

BACKGROUND ART

Conventionally, excrement (feces and urine) of livestock such as cows is piled and treated in a compost shed located near a cattle barn. However, when fermentation does not progress as expected, an excess amount of excrement may be piled and urine may seep out of the shed. Furthermore, treatment of this large amount of compost may require large costs.

The applicant of the present invention has already filed, as exemplarily listed below as Patent Document 1, a patent application related to reduced-pressure fermentation drying equipment configured to: store organic waste in an airtight container such as a tank; heat and stir the content under reduced pressure so that the temperature of the waste is within a predetermined temperature range in order to dry the waste by efficiently evaporating water; and improve fermentation of organic matter contained in the organic waste to be treated by adding prescribed microorganisms thereto.

PRIOR ART DOCUMENTS

Patent Documents

Patent Document 1: JP 2007-319738 A
Patent Document 2: JP 4153685

SUMMARY OF THE INVENTION

Problem to be Solved by the Invention

The present invention was made in consideration of the above circumstances, an object of which is to provide a treatment system and a treatment method for effectively decomposing, by microorganisms, organic matter contained in excrement of livestock to promote fermentation, and furthermore using obtained product as fuel.

Means for Solving the Problem

In order to solve the above problems, the present invention provides a system for treating excrement of livestock having the following configuration. That is, the system of the present invention includes: reduced-pressure fermentation drying equipment that stores excrement of livestock in an airtight container, heats and stirs the excrement of livestock under reduced pressure so that a temperature of the excrement of livestock is within a predetermined temperature range, decomposes organic components of organic matter using microorganisms, and obtains volume-reduced dried product; and heat source equipment that is provided on a downstream side of the reduced-pressure fermentation drying equipment and generates a heat source by combusting the obtained volume-reduced dried product.

With the present invention, the excrement of livestock can be efficiently fermented and its volume can be reduced by the reduced-pressure fermentation drying equipment. Thus, it is possible to significantly reduce costs of treating the excrement of livestock. Also, a heat source can be generated by the heat source equipment using, as fuel, the product (dried product) obtained by the reduced-pressure fermentation drying equipment. Thus, by making good use of the product, it is possible to generate the heat source such as steam while hardly generating waste.

In the present invention, it is preferable that the reduced-pressure fermentation drying equipment includes at least two primary reduced-pressure fermentation dryers and at least one secondary reduced-pressure fermentation dryer that is provided on the downstream side of the at least two primary reduced-pressure fermentation dryers. It is also preferable that the installation number of the secondary reduced-pressure fermentation dryers is equal to or less than the installation number of the at least two primary reduced-pressure fermentation dryers. With this configuration, it is possible to reduce the installation number of the secondary reduced-pressure fermentation dryers, which also leads to reduction in installation space and thus reduction in the running cost.

In the present invention, it is preferable that part of the heat source generated by the heat source equipment is used at least by the reduced-pressure fermentation drying equipment. With this configuration, there is no need to provide, for example, a steam boiler or the like in the reduced-pressure fermentation drying equipment, which results in a simple configuration of the system and also reduction in the running cost.

In the present invention, it is preferable to further include a generator that is provided on the downstream side of the heat source equipment so as to receive part of the generated heat source to generate electric power. With this configuration, it is possible to convert the generated heat source into electric power.

In the present invention, it is preferable that the electric power obtained by the generator is used by the reduced-pressure fermentation drying equipment. With this configuration, it is possible to cover part of the electric power that is consumed by the reduced-pressure fermentation drying equipment by power generation of the generator, which also leads to reduction in the running cost.

In the present invention, it is preferable that the excrement of livestock is transported from a livestock barn by a tank truck so as to be stored in the airtight container of the reduced-pressure fermentation drying equipment. With this configuration, there is no need to install conveyance equipment such as conveyors even when the treatment system is disposed far from the livestock barn, which results in a simple configuration of the system and also reduction in the running cost.

Also, the present invention provides a method for treating excrement of livestock that includes: a reduced-pressure fermentation drying step of storing excrement of livestock in an airtight container, heating and stirring the excrement of livestock under reduced pressure so that a temperature of the excrement of livestock is within a predetermined temperature range, decomposing organic components of organic matter using microorganisms, and obtaining volume-reduced dried product; and a heat source generation step of generating a heat source by combusting the volume-reduced dried product obtained in the reduced-pressure fermentation drying step. With this method, it is possible to expect the same effects as those obtained in the system for treating excrement of livestock.

Effect of the Invention

With the system and the method for treating excrement of livestock of the present invention, it is possible to significantly reduce costs of treating the excrement of livestock. Also, by making good use of the product of the reduced-pressure fermentation drying equipment, it is possible to generate the heat source while hardly generating waste. Furthermore, it is possible to reduce the installation space and thus the running cost by decreasing the installation number of the secondary reduced-pressure fermentation dryers.

MODE FOR CARRYING OUT THE INVENTION

Figure 1:
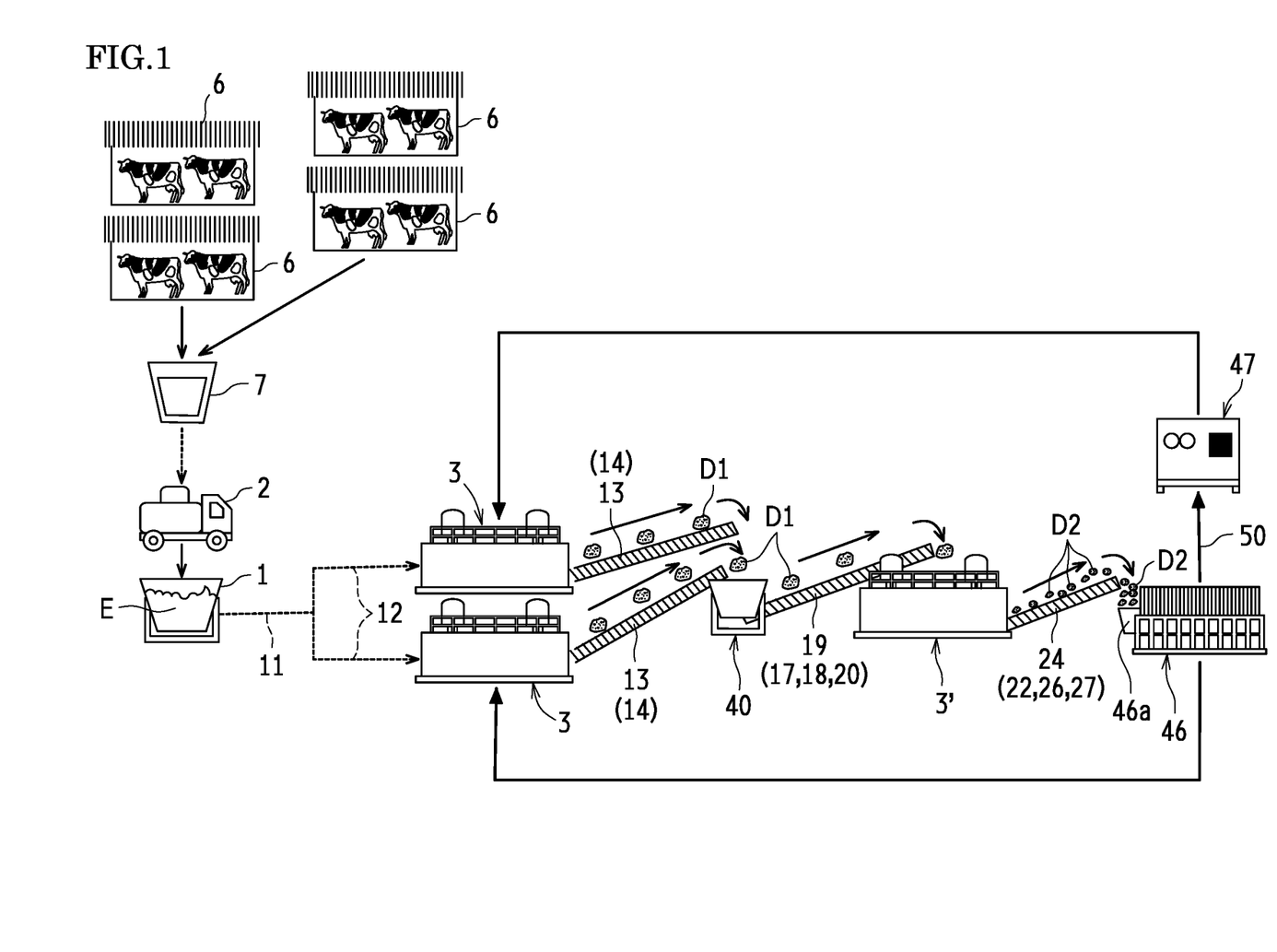
FIG. 1 is a diagram schematically illustrating a system for treating excrement of livestock according to an embodiment of the present invention.
Figure 2:
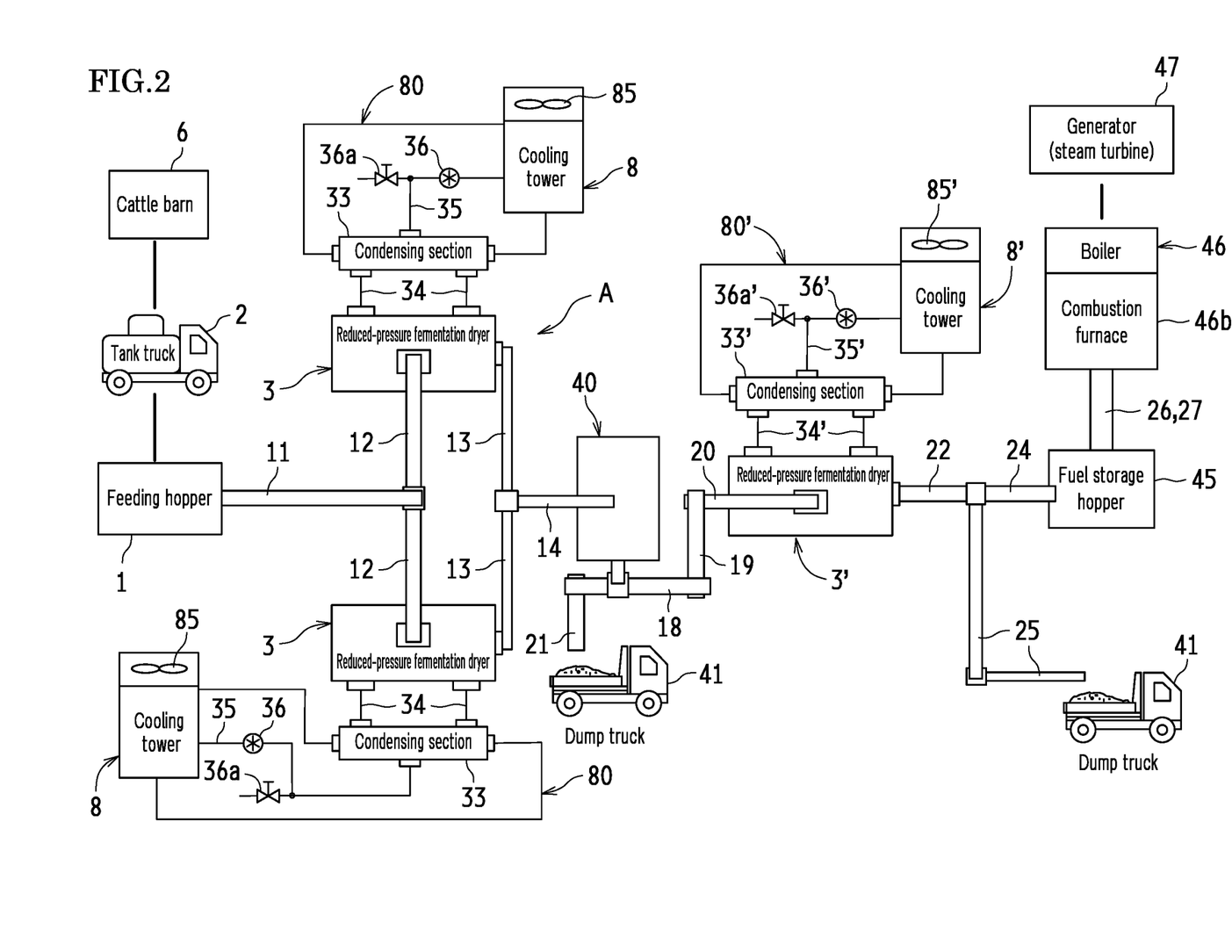
FIG. 2 is a diagram schematically illustrating a configuration of the system.
Figure 3:
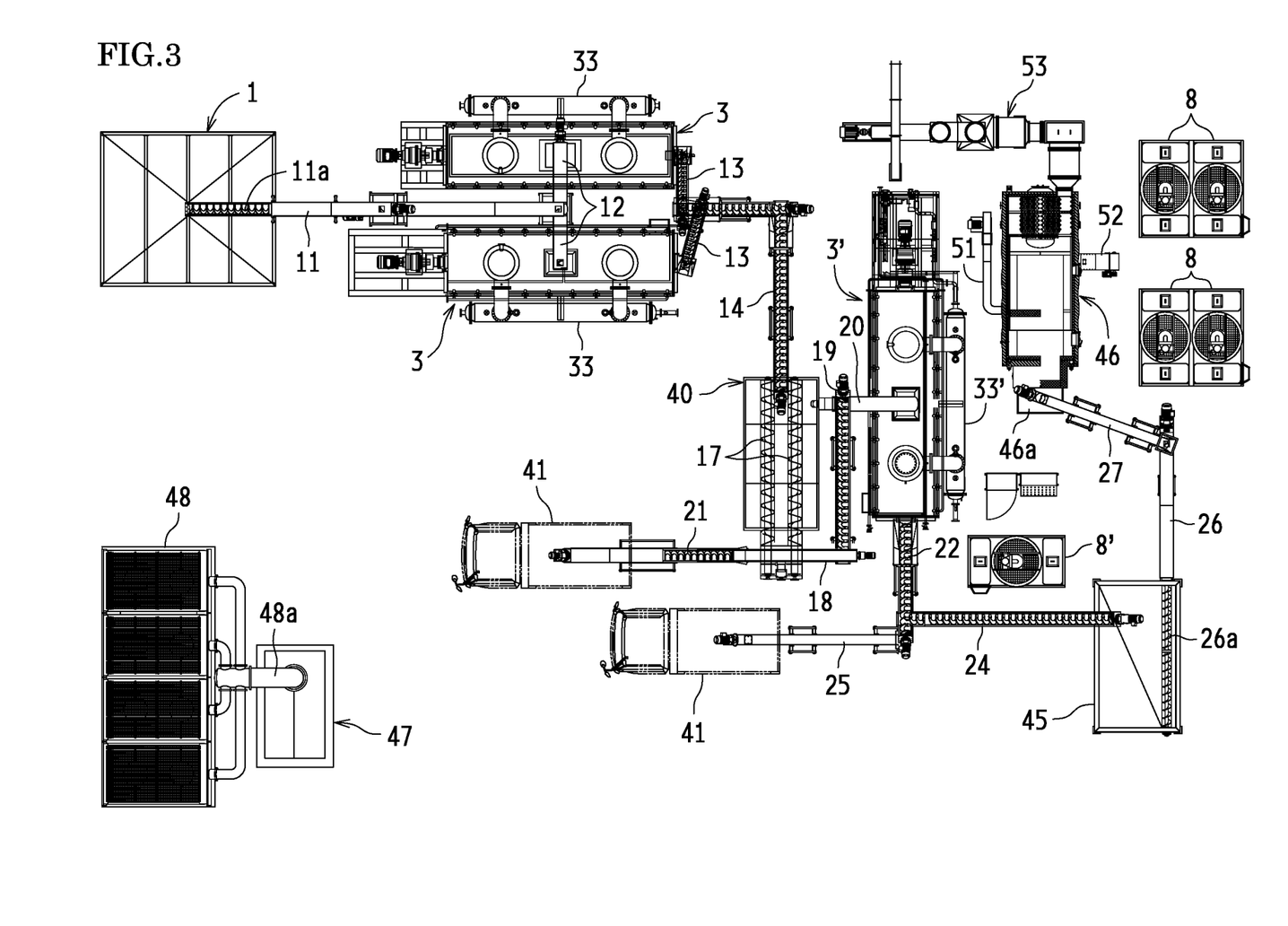
FIG. 3 is a plan view specifically illustrating an overall configuration of the system.

Hereinafter, an embodiment of the present invention will be described with reference to the drawings. FIG. 1 is a diagram schematically illustrating a system for treating excrement of livestock according to the embodiment of the present invention. FIG. 2 is a diagram schematically illustrating a configuration of the system. FIG. 3 is a plan view specifically illustrating an overall configuration of the system.

In FIGS. 1 to 3, a feeding hopper 1 stores excrement (feces and urine) E of livestock as an object to be treated. Here, the livestock means, for example, cows, pigs, sheep and chickens, but is not particularly limited thereto. In this embodiment, a description is given on excrement of cows as an object to be treated. Slurry waste stored in a tank of a tank truck 2 is discharged into the feeding hopper 1 by reverse rotation of a vacuum pump built in the tank truck 2. The slurry waste of cows is raked up from a plurality of (four in FIG. 1) cattle barns 6 and collected in a storage hopper 7. The excrement in the storage hopper 7 is sucked up in the tank of the tank truck 2 by vacuum suction caused by forward rotation of the built-in vacuum pump. When the tank truck 2 sucks up the excrement in the storage hopper 7 into the tank and transports it to the feeding hopper 1, the excrement of cows in the cattle barns 6 is newly collected in the storage hopper 7, and this series of operations is repeatedly performed. In this embodiment, the tank truck 2 is used as means of transport from the cattle barns 6 to the feeding hopper 1. However, when the cattle barns 6 and the feeding hopper 1 are located close to each other, a carrying-out conveyor may be provided in place of using the tank truck 2, which can reduce the running cost.

The capacity of cattle barns (livestock barns) 6 may be, in total, 1,000 milk cows. Slurry waste of these milk cows is repeatedly recovered and collected in the storage hopper 7. The storage hopper 7 may store, as the waste of 1,000 milk cows, about 60 tons of excrement per day. This slurry waste contains approximately 87 to 90% water.

The excrement E fed into the feeding hopper 1 is supplied to reduced-pressure fermentation drying equipment A. In this embodiment, the reduced-pressure fermentation drying equipment A is constituted of two primary reduced-pressure fermentation dryers 3 and one secondary reduced-pressure fermentation dryer 3'.

The two primary reduced-pressure fermentation dryers 3 treat, in total, almost all the excrement (approximately 60 tons) per day from the cattle barns 6, and discharge thus treated waste as primary dried product. The moisture content of this primary dried product D1 is substantially 60%. The amount of waste per day (about 60 tons) from the cattle barns 6 and the moisture content of the primary dried product D1 (about 60%) are shown here as an example. The installation number of the primary reduced-pressure fermentation dryers 3 may be appropriately defined so as to reliably treat the waste per day from the cattle barns 6 to discharge it as the primary dried product D1 with a predetermined moisture content.

Figure 4:
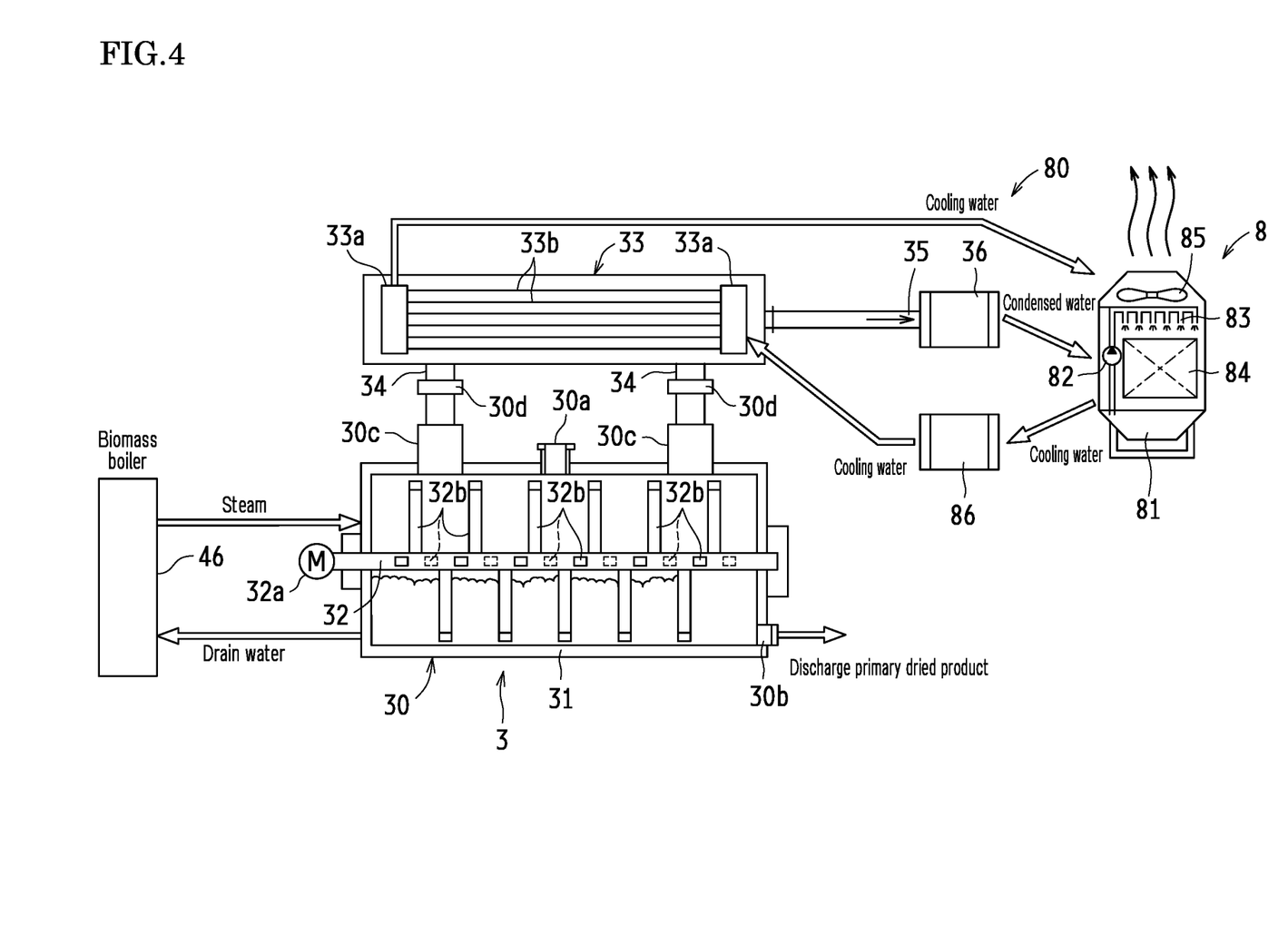
FIG. 4 is a diagram schematically illustrating a configuration of a primary reduced-pressure fermentation dryer provided in the system.

The two primary reduced-pressure fermentation dryers 3, which are provided in the reduced-pressure fermentation drying equipment A, have the same configuration. Thus, the configuration of one of them is described in detail. FIG. 4 is a diagram schematically illustrating the configuration of the primary reduced-pressure fermentation dryer 3. As shown in FIGS. 1 to 3, the excrement E is distributed to the two primary reduced-pressure fermentation dryers 3 from the feeding hopper 1 via a feeding conveyor 11 and dividing conveyors 12 disposed in the other end of the feeding conveyor 11. As shown in FIG. 3, the feeding conveyor 11 includes a screw 11a that carries out the excrement E in the feeding hopper 1 diagonally upward from the bottom. As shown in FIG. 4, the primary reduced-pressure fermentation dryer 3 includes, as an airtight container to store the excrement E supplied from the dividing conveyor 12, a substantially cylinder-shaped tank (pressure-resistant tank, i.e. airtight container) 30 formed to have airtightness such that the pressure inside the tank 30 is maintained equal to or lower than the atmospheric pressure. A heating jacket 31 is provided on a peripheral wall part of the tank 30. The heating jacket 31 receives steam for heating that is generated in a biomass boiler 46 (described later). The temperature of the steam supplied from the biomass boiler 46 is preferably about 140° C. Since a suction effect also acts on the feeding conveyor 11 and the dividing conveyors 12 due to decompression by the primary reduced-pressure fermentation dryer 3, the slurry excrement E can be easier conveyed.

In the tank 30, a stirring shaft 32 is disposed so as to extend in the longitudinal direction (left and right direction in FIG. 4) while it is surrounded by the heating jacket 31. The stirring shaft 32 is rotated by an electric motor 32a at a predetermined rotational speed. The stirring shaft 32 includes a plurality of stirring blades 32b that is separated from each other in the shaft direction. The stirring blades 32b stir the excrement E so that the excrement E is primarily fermented and dried, and then transported as the primary dried product D1 in the longitudinal direction of the tank 30.

A feeding hole 30a for the excrement E is provided in an upper part of the tank 30. The excrement E that is fed through the feeding hole 30a is heated by the heating jacket 31 while stirred by the rotation of the stirring shaft 32. After elapse of a predetermined period of time, the primary dried product D1 is discharged from a discharge section 30b provided in a lower part of a back wall of the tank 30. In place of the electric motor 32a, a hydraulic motor may be used.

On the upper part of the tank 30, a guiding section 30c, which guides steam generated from the heated excrement E to a condensing section 33, is provided so as to protrude from the tank 30. The condensing section 33 is supported by a communication passage 34 via the guiding section 30c. In the condensing section 33, a plurality of cooling tubes 33b is provided so as to be held by a pair of heads 33a. A cooling channel 80 is provided between the plurality of cooling tubes 33b and a cooling tower 8. In this embodiment, the condensing section 33 extends parallel to the longitudinal direction of the tank 30, and is provided backward the guiding section 30c. In the schematic view in FIG. 4, only one cooling tower 8 is illustrated. However, as it can be seen from the specific plan view in FIG. 3, two cooling towers 8 are provided for one primary reduced-pressure fermentation dryer 3 in order to enhance the cooling effect. Thus, four cooling towers 8 are provided in total.

In the condensing section 33, the temperature of cooling water is increased by heat exchange with hot steam during passing through the cooling tubes 33b. The cooling water with increased temperature passes through the cooling channel 80 to flow into a water receiving tank 81 of the cooling tower 8, as schematically shown by the arrow in FIG. 4. The cooling tower 8 includes: a drawing pump 82 that draws the cooling water from the water receiving tank 81; and a nozzle 83 that sprays the drawn cooling water. The cooling water sprayed from the nozzle 83 flows downward through a downward flowing section 84 with being blown by a fan 85, which lowers the temperature of the cooling water. Then, the cooling water flows again into the water receiving tank 81.

The cooling water cooled by the cooling tower 8 is transported by a cooling water pump 86 and is supplied to the condensing section 33 via the cooling channel 80. During passing through the plurality of cooling tubes 33b, the temperature of the cooling water is increased by heat exchange with steam generated in the tank 30 as described above. After that, the cooling water once again flows into the water receiving tank 81 of the cooling tower 8 via the cooling channel 80. That is, the cooling water circulates through the cooling channel 80 between the condensing section 33 and the cooling tower 8.

Apart from the cooling water that circulates as described above, condensed water also flows into the cooling tower 8, which is condensed from the steam generated from the heated excrement E in the condensing section 33. Although it is omitted from the drawings, the condensed water generated by the heat exchange with the hot steam is gathered in a bottom part of the condensing section 33.

A vacuum pump 36 is connected to the condensing section 33 via a communication passage 35 so as to reduce the pressure in the tank 30. Thus, when the vacuum pump 36 operates, air and condensed water are sucked from the condensing section 33 via the communication passage 35, and furthermore air and condensed water in the tank 30 are sucked via the communication passage 34 and the guiding section 30c. Accordingly, the condensed water is sucked from the condensing section 33 by the vacuum pump 36, and guided from the vacuum pump 36 to the water receiving tank 81 of the cooling tower 8 via a water conduit. An on-off valve 30d is provided on the communication passage 34, which prevents air and the like from being sucked from the primary reduced-pressure fermentation dryer 3 when it is stopped.

Then, the condensed water introduced in the water receiving tank 81 of the cooling tower 8 is mixed with the cooling water. The mixed cooling water is drawn, as described above, by the drawing pump 82 so as to be sprayed by the nozzle 83. After being sprayed, the cooling water flows downward through the downward flowing section 84 while being cooled. Since the condensed water contains the same microorganisms as those added in the tank 30, an odor component or the like contained in the condensed water has been decomposed. Thus, the odor of the air is not diffused outside the tank when it is exhausted by the fan 85.

Here, operations of the above-configured primary reduced-pressure fermentation dryer 3 are described. The excrement E stored in the tank 30 is heated by the steam for heating that is supplied to the heating jacket 31 while being stirred by the rotation of the stirring shaft 32. The excrement E is heated from the outside by the heating jacket 31 surrounding the inside of the tank 30 as well as heated from the inside by the stirring shaft 32 and the like. Thus, the temperature of the excrement E in the tank 30 is effectively increased while the excrement E is stirred by the stirring shaft 32. Furthermore, since the pressure in the tank 30 is reduced due to operations of the vacuum pump 36, the boiling point is reduced in the tank 30. As a result, the water evaporates in the temperature range in which decomposition of organic components contained in the excrement E is promoted by the microorganisms.

It is preferable that the reduced-pressure fermentation drying step by the primary reduced-pressure fermentation dryer 3 takes, for example, 24 hours as one process (one cycle). First, the excrement E is fed for 30 minutes. Then the organic components contained in the excrement E are decomposed in the fermentation step while the excrement E is dried in the dry step. Both steps concurrently continue for 23 hours. After that, the primary dried product D1 (containing about 60% water) is discharged for 30 minutes. During this cycle, the inside of the tank 30 is decompressed to −0.06 to −0.07 MPa (gauge pressure, hereinafter this unit name is omitted), so that the water temperature inside the tank 30 is maintained at 76 to 69° C. (saturated steam temperature). As a result, the primary fermentation, decomposition and drying of the excrement E are promoted by the microorganisms described later.

Now, a description is given on conveyance of the primary dried product D1 from the primary reduced-pressure fermentation dryers 3 to the secondary reduced-pressure fermentation dryer 3'. The discharge sections 30b of the primary reduced-pressure fermentation dryers 3 are respectively connected to carrying-out branch conveyors 13. These two carrying-out branch conveyors 13 join one carrying-out collection conveyor 14. The carrying-out collection conveyor 14 makes a right-angled turn. As shown in FIG. 3, a screw conveyor is adopted to each of the carrying-out branch conveyors 13 and the carrying-out collection conveyor 14 so as to carry out the primary dried product D1 having viscosity.

As shown in FIG. 3, the carrying-out collection conveyor 14 extends in the right direction in the figure and then bends downward to be connected to a secondary feeding hopper 40 such that the carrying-out collection conveyor 14 feeds the primary dried product D1 into the secondary feeding hopper 40 from above. In this way, the primary dried product D1 that is conveyed from the primary reduced-pressure fermentation dryers 3 is once stored in the secondary feeding hopper 40. The secondary feeding hopper 40 tapers toward the bottom on which two lines of secondary transport conveyors 17 are provided. The primary dried product D1 is carried out from the bottom part of the secondary feeding hopper 40 toward the outside (downward in FIG. 3) by driving the secondary transport conveyors 17. Furthermore, a secondary carrying-out conveyor 18, which extends in the left and right direction in FIG. 3, is connected to the lower part of the secondary feeding hopper 40 (see FIG. 3). A secondary feeding conveyor 19 and further a direction changing conveyor 20 are connected to one end of the secondary carrying-out conveyor 18 (right end in FIG. 3). The secondary feeding conveyor 19 is disposed along the secondary feeding hopper 40, and the direction changing conveyor 20 is connected to an end of the secondary feeding conveyor 19. The primary dried product D1 in the secondary feeding hopper 40 is fed into the secondary reduced-pressure fermentation dryer 3' via the direction changing conveyor 20. After elapse of a predetermined period of time, secondary dried product D2 can be discharged from a discharge section 30'b of the secondary reduced-pressure fermentation dryer 3'. In the other end of the secondary carrying-out conveyor 18 (left end in FIG. 3), a branch conveyor 21 for discharge is provided so as to convey the primary dried product D1 having viscosity. Thus, when the secondary carrying-out conveyor 18 is inversely driven, it is possible to carry out the primary dried product D1 having viscosity to a loading platform of a dump truck 41, from the other end of the secondary carrying-out conveyor 18 via the branch conveyor 21 for discharge.

The secondary reduced-pressure fermentation dryer 3' has almost the same configuration as the primary reduced-pressure fermentation dryer 3. Thus, the reference numeral 3' is assigned to it and the detail description thereof is omitted. As shown in FIG. 3, the secondary reduced-pressure fermentation dryer 3' has only one cooling tower 8'.

The reduced-pressure fermentation drying step by the secondary reduced-pressure fermentation dryer 3' is also almost the same as that by the primary reduced-pressure fermentation dryer 3. That is, the primary dried product D1 is fed into a tank 30' for 30 minutes. Then, similarly to the above, unfermented organic matter contained in the primary dried product D1 is fermented and further dried for 23 hours. During this cycle, the inside of the tank 30' is decompressed to −0.09 to −0.10 MPa, so that the water temperature inside the tank 30' is maintained at 46 to 42° C. (saturated steam temperature). As a result, the secondary fermentation, decomposition and drying of the primary dried product D1 are promoted by the microorganisms described later. In this way, it is possible to discharge secondary dried product D2 (containing about 15% water) from the discharge section 30'b of the secondary reduced-pressure fermentation dryer 3'.

As to the microorganisms added to the organic matter in the tanks 30 and 30' at the time of drying treatment, it is preferable to use complex effective microorganisms, which are cultured in advance using a plurality of kinds of native microorganisms as a base, as described, for example, in Patent Document 2. That is, groups of so-called SHIMOSE 1, SHIMOSE 2 and SHIMOSE 3 have the majority of the colony.

Here, SHIMOSE 1 has the accession number FERM BP-7504 (internationally deposited with the Patent Microorganisms Depository of the National Institute of Advanced Industrial Science and Technology and the National Institute of Bioscience and Human-Technology of the Ministry of Economy, Trade and Industry (1-1-3 Higashi, Tsukuba, Ibaraki, Japan) on Mar. 14, 2003). Also, SHIMOSE 2 has the accession number FERM BP-7505 (internationally deposited in the same manner as SHIMOSE 1), which is a microorganism belonging to the genus *Pichiafarinosa* having salt tolerance. SHIMOSE 3 has the accession number FERM BP-7506 (internationally deposited in the same manner as SHIMOSE 1), which is a microorganism belonging to the genus *Staphylococcus*.

Here, a description is given on how to proceed with the reduced-pressure fermentation drying of the organic matter by the primary reduced-pressure fermentation dryer 3. First, the excrement E stored in the feeding hopper 1 is fed into the feeding hole 30a of the tank 30 of the primary reduced-pressure fermentation dryer 3. Then, the tank 30 is sealed so that the inside of the tank 30 is kept at the atmospheric pressure.

After adding the prescribed microorganisms to the excrement E in the tank 30, the tank 30 is sealed by closing an atmosphere opening valve 36a disposed in the vicinity of the vacuum pump 36. Thus, the inside of the tank 30 is heated under reduced pressure so that the organic components of the excrement E in the tank 30 is primarily fermented and dried. Specifically, the inside of the tank 30 is heated by the steam for heating that is supplied from the biomass boiler 46 described later.

The inside of the tank 30 is heated by the steam for heating as described above while the stirring shaft 32 is rotated at a predetermined rotational speed (for example, about 8 rpm). Furthermore, the pressure in the tank 30 is reduced by operating the vacuum pump 36. Thus, the temperature inside the tank 30 is optimized for microbial activity. As a result, decomposition of the organic components of the organic matter is effectively promoted by the microorganisms. Here, the rotational speed (8 rpm) of the stirring shaft 32 is shown as an example, and any other rotational speed may be adopted to the extent that the organic components of the organic matter can be decomposed.

When a predetermined period of time is elapsed in the state in which the temperature and the pressure in the tank 30 are maintained, the vacuum pump 36 and the supply of steam for heating from the biomass boiler 46 are stopped, while the atmosphere opening valve 36a is opened, so that the pressure inside the tank 30 becomes the atmospheric pressure. Furthermore, the stirring shaft 32 is reversely rotated and the lid of the discharge section 30b of the tank 30 is opened so as to discharge the primary dried product D1 from the tank 30. At that time, the volume of the primary dried product D1 that is discharged from the tank 30 has been reduced.

Next, the primary dried product D1 in the secondary feeding hopper 40 is fed into the secondary reduced-pressure fermentation dryer 3'. Since how to proceed with the secondary reduced-pressure fermentation drying of the primary dried product D1 is almost the same as the primary reduced-pressure fermentation drying step, a detail description thereof is omitted here. In this way, it is possible to discharge the secondary dried product D2 from the discharge section 30'b of the secondary reduced-pressure fermentation dryer 3'. The volume of the secondary dried product D2 has been further reduced than the primary dried product D1.

The secondary reduced-pressure fermentation dryer 3' is connected to a biomass fuel storage hopper 45 via a secondary dried product carrying-out conveyor 22 extending downward in FIG. 3 and a direction changing conveyor 24 connected to a lower end of the secondary dried product carrying-out conveyor 22. The secondary dried product D2 obtained by the secondary reduced-pressure fermentation dryer 3' is once stored in the biomass fuel storage hopper 45 as biomass fuel. The secondary dried product carrying-out conveyor 22 and the direction changing conveyor 24 are each constituted of a screw conveyor such that the secondary dried product D2, which is discharged from the discharge section 30'b disposed in the lower part of the tank 30' of the secondary reduced-pressure fermentation dryer 3', is conveyed to a higher position than the discharge section 30'b. Furthermore, a secondary carrying-out branch conveyor 25 is connected to an end (a lower end in FIG. 3) of the secondary dried product carrying-out conveyor 22. By this secondary carrying-out branch conveyor 25, the secondary dried product D2 can be discharged into the platform of the dump truck 41.

The dump truck 41 transports the secondary dried product D2 discharged from the secondary reduced-pressure fermentation dryer 3' and the primary dried product D1 stored in the secondary feeding hopper 40 to the cattle barns 6 so as to spread the secondary dried product D2 and the primary dried product D1 on the excrement E accumulated in the cattle barns 6 and/or on the excrement accumulated in the compost shed in the case where it is located in the vicinity of the cattle barns 6. Thus, fermentation of the excrement is promoted and the volume of the excrement is reduced.

The biomass fuel storage hopper 45 is connected to the biomass boiler 46 via a biomass fuel carrying-out conveyor 26 which extends upward in FIG. 3 and a direction changing conveyor 27 for biomass fuel which extends diagonally leftward from this fuel carrying-out conveyor 26 in FIG. 3. The biomass fuel carrying-out conveyor 26 includes, on one end thereof (a lower end in FIG. 3), a screw 26a that conveys the biomass fuel (secondary dried product D2) that exists in the bottom of the biomass fuel storage hopper 45, from the bottom to the upper part.

The biomass boiler 46 generates steam as a heat source by combusting the secondary dried product D2 as biomass fuel, which is obtained by the secondary reduced-pressure fermentation dryer 3'. That is, the biomass boiler 46 performs a heat source generation step of generating steam (heat source) by combusting, as biomass fuel, the secondary dried product D2 that is obtained in a secondary reduced-pressure fermentation drying step using the secondary reduced-pressure fermentation dryer 3'.

The biomass boiler 46 is provided on the right side of the secondary reduced-pressure fermentation dryer 3' in FIG. 3. Also in FIG. 3, the biomass boiler 46 includes a storage section 46a in a lower end thereof, which stores biomass fuel. In the biomass boiler 46, the biomass fuel stored in the storage section 46a is fed into a combustion furnace 46b so as to be combusted in the combustion furnace 46b. Thus, combustion gas is generated. Water that supplied via a water passage 51 flows around the combustion furnace 46b of the biomass boiler 46. This water is heated by the combustion gas generated in the combustion furnace 46b to generate steam at high temperature and high pressure. The temperature of the generated steam is, for example, about 185° C. A conveyor 52 for carrying out ashes is connected to the biomass boiler 46 so that ashes after combustion of the biomass fuel are carried out.

As shown in FIG. 1, part of the steam generated in the biomass boiler 46 is supplied to the two primary reduced-pressure fermentation dryers 3, and passes through the respective heating jackets 31 of the tanks 30 of the primary reduced-pressure fermentation dryers 3 so as to heat the insides of the tanks 30. Thus, it is possible to generate the steam for heating the excrement E, which is necessary in the respective primary reduced-pressure fermentation dryers 3, by use of the secondary dried product D2 discharged from the secondary reduced-pressure fermentation dryer 3'. As a result, it is possible to reduce the overall running cost of the system for treating the excrement of livestock. In addition, the steam generated in the biomass boiler 46 may naturally be used by the secondary reduced-pressure fermentation dryer 3'.

Furthermore, a steam turbine generator 47 is connected to the biomass boiler 46 via a steam passage 50 through which the rest of the generated steam passes. The steam turbine generator (generator) 47 includes a steam turbine in the inside (not shown). The steam at high temperature and high pressure flows from the biomass boiler 46 via the steam passage 50 toward an impeller of the steam turbine. Thus, the steam turbine is rotated at a high speed to generate electric power. As shown in FIG. 3, a heat exchanger 48 is connected to the steam turbine generator 47 via a steam pipe 48a. The heat exchanger 48 cools the steam for heating that is supplied from the steam turbine generator 47 via the steam pipe 48a. Although it is not shown in the drawings, condensed water obtained by cooling is, for example, returned to the biomass boiler 46 so as to be used to generate the steam for heating the excrement E. As to exhaust gas from the combustion furnace 46b, it is released to the atmospheric air after eliminating the possibility of environmental pollution using an exhaust gas treatment device 53.

As shown in FIG. 1, the electric power generated by the steam turbine generator 47 is supplied to the two primary reduced-pressure fermentation dryers 3. Thus, the electric power generated by the steam turbine generator 47 can be used as part of electric power required to operate the primary reduced-pressure fermentation dryers 3. Thus, it is possible to further reduce the overall running cost of the system for treating the excrement of livestock. The electric power generated by the steam turbine generator 47 may also be used by the secondary reduced-pressure fermentation dryer 3', and surplus power, if any, may be supplied to the other equipment. Furthermore, when there still remains surplus power, it is possible to sell such surplus power to an electric power company.

In this embodiment, it is thus possible to ferment the excrement E (60 tons per day, containing 87 to 90% water) that is discharged from the cattle barns 6 by the two primary reduced-pressure fermentation dryers 3 and also the one secondary reduced-pressure fermentation dryer 3' of the reduced-pressure fermentation drying equipment A so as to produce the secondary dried product D2 whose volume is significantly reduced (containing approximately 15% water). Furthermore, the secondary dried product D2 is combusted as biomass fuel in the biomass boiler 46 and reduced to ashes. Thus, only a small amount of industrial waste is generated, which requires reduced processing costs. In addition, all the excrement E discharged from the cattle barns 6 and the compost shed can be reduced to ashes, which results in no compost shed being needed. Therefore, a site for the compost shed can be used to construct cattle barns, and accordingly the number of milk cows can be increased.

Since the secondary reduced-pressure fermentation dryer 3' ferments and dries the primary dried product D1 whose volume has been already reduced by the two primary reduced-pressure fermentation dryers 3, the installation number of the secondary reduced-pressure fermentation dryers 3' can be less than the installation number of the primary reduced-pressure fermentation dryers 3. Therefore, it is possible to reduce the installation space for the reduced-pressure fermentation drying equipment A and thus reduce the running cost. In this embodiment as disclosed above, the description was given on the case in which the system includes two primary reduced-pressure fermentation dryers 3 and one secondary reduced-pressure fermentation dryer 3'. However, the installation number of these dryers may be appropriately determine according to the treatment amount of excrement.

Furthermore, the secondary dried product D2 discharged from the secondary reduced-pressure fermentation dryer 3' is used as biomass fuel in the biomass boiler 46 so as to generate steam as a heat source for the tank 30 of the primary reduced-pressure fermentation dryer 3. In this way, it is possible to generate the heat source (steam) while hardly generating waste.

The foregoing embodiment is to be considered in all respects as illustrative and not limiting. The scope of the invention is indicated by the appended claims rather than by the foregoing embodiment, and all modifications and changes that come within the meaning and range of equivalency of the claims are intended to be embraced therein.

This application claims priority based on Patent Application No. 2018-200659 filed in Japan on Oct. 25, 2018. The entire contents thereof are hereby incorporated in this application by reference.

INDUSTRIAL APPLICABILITY

The present invention is suitably applied to a system and a method for treating excrement of livestock.

DESCRIPTION OF REFERENCE NUMERALS

2 Tank truck
6 Cattle barn (livestock barn)
A Reduced-pressure fermentation drying equipment
3 Primary reduced-pressure fermentation dryer
3' Secondary reduced-pressure fermentation dryer
30 Tank (airtight container)
46 Biomass boiler (heat source equipment)
47 Steam turbine generator (generator)

The invention claimed is:

1. A system for treating excrement of livestock, comprising:
reduced-pressure fermentation drying equipment configured to: store excrement of livestock in an airtight container; heat and stir the excrement of livestock under reduced pressure that is below atmospheric pressure gauge so that a temperature of the excrement of livestock is within a predetermined temperature range; decompose organic components of organic matter using microorganisms; and obtain volume-reduced dried product; and
heat source equipment provided on a downstream side of the reduced-pressure fermentation drying equipment, the heat source equipment generating a heat source by combusting the obtained volume-reduced dried product, wherein
the reduced-pressure fermentation drying equipment includes:
at least two primary reduced-pressure fermentation dryers; and
at least one secondary reduced-pressure fermentation dryer provided on a downstream side of the at least two primary reduced-pressure fermentation dryers, wherein an installation number of the at least one secondary reduced-pressure fermentation dryer is equal to or less than an installation number of the at least two primary reduced-pressure fermentation dryers,
a hopper is provided between the at least two primary reduced-pressure fermentation dryers and the at least one secondary reduced-pressure fermentation dryer, and
primary dried product discharged from the at least two primary reduced-pressure fermentation dryers is collected and once stored in the hopper, and then is fed into the at least one secondary reduced-pressure fermentation dryer.

2. The system for treating excrement of livestock according to claim 1, wherein
part of the heat source generated by the heat source equipment is used by the reduced-pressure fermentation drying equipment.

3. The system for treating excrement of livestock according to claim 1, further comprising a generator connected to the heat source equipment so as to receive part of the generated heat source to generate electric power.

4. The system for treating excrement of livestock according to claim 3, wherein
the electric power obtained by the generator is used by the reduced-pressure fermentation drying equipment.

5. The system for treating excrement of livestock according to claim 1, wherein
the excrement of livestock is transported from a livestock barn by a tank truck so as to be stored in the airtight container of the reduced-pressure fermentation drying equipment.

6. The system for treating excrement of livestock according to claim 1, wherein
a carrying-out conveyor and a feeding conveyor are provided between the hopper and the at least one secondary reduced-pressure fermentation dryer, and
the carrying-out conveyor carries out the primary dried product from the hopper, and the feeding conveyor feeds the primary dried product carried out by the carrying-out conveyor into the at least one secondary reduced-pressure fermentation dryer.

7. The system for treating excrement of livestock according to claim 6, wherein
a secondary carrying-out conveyor, a secondary feeding conveyor, and a direction changing conveyer are provided between a secondary feeding hopper and the at least one secondary reduced-pressure fermentation dryer, and
the secondary carrying-out conveyor carries out the primary dried product from the secondary feeding hopper, and the secondary feeding conveyor feeds:
a) the primary dried product carried out by the secondary carrying-out conveyor into the at least one secondary reduced-pressure fermentation dryer via the direction changing conveyer, or
b) a primary dried product having viscosity into a branch convey for discharge.

8. A method for treating excrement of livestock by using the system for treating excrement of livestock recited in claim 1, comprising:
a reduced-pressure fermentation drying step of: storing excrement of livestock in an airtight container; heating and stirring the excrement of livestock under reduced pressure so that a temperature of the excrement of livestock is within a predetermined temperature range; decomposing organic components of organic matter using microorganisms; and obtaining volume-reduced dried product; and
a heat source generation step of generating a heat source by combusting the volume-reduced dried product obtained in the reduced-pressure fermentation drying step.

* * * * *